United States Patent [19]

Schindele

[11] Patent Number: 5,048,539

[45] Date of Patent: Sep. 17, 1991

[54] METHODS AND APPARATUS FOR DIRECTLY SENSING AND MEASURING BLOOD RELATED PARAMETERS

[75] Inventor: Gary M. Schindele, Fairfield, Conn.

[73] Assignee: Medical Systems Development Corporation, Fairfield, Conn.

[21] Appl. No.: 639,504

[22] Filed: Sep. 28, 1990

Related U.S. Application Data

[63] Continuation of Ser. No. 547,381, Jul. 3, 1990, which is a continuation of Ser. No. 264,614, Oct. 31, 1988, abandoned.

[51] Int. Cl.⁵ ............................................. A61B 5/00
[52] U.S. Cl. .................................... 128/771; 204/403
[58] Field of Search ............... 128/635, 760, 763, 771; 604/403; 204/403; 436/16, 68, 74

[56] References Cited

U.S. PATENT DOCUMENTS

| | | | |
|---|---|---|---|
| 3,512,517 | 5/1970 | Kadish et al. | 128/635 |
| 3,661,010 | 5/1972 | Neuwelt | 128/635 |
| 3,920,396 | 11/1975 | Schuy | 436/68 |
| 4,040,908 | 8/1977 | Clark | 204/403 |
| 4,272,245 | 6/1981 | Diamond et al. | 436/68 |
| 4,339,317 | 7/1982 | Meiattini et al. | 204/403 |
| 4,418,703 | 12/1983 | Hoch et al. | 128/763 |
| 4,478,222 | 10/1984 | Koning et al. | 128/635 |
| 4,535,786 | 8/1985 | Kater | 128/760 |
| 4,791,938 | 12/1988 | Van Valkenburg | 128/763 |
| 4,852,548 | 8/1989 | Selby | 604/403 |

Primary Examiner—Max Hindenburg
Attorney, Agent, or Firm—Joseph J. Kaliko

[57] ABSTRACT

A disposable cartridge, included in a blood sample analysis system, is described wherein the cartridge itself contains means for both sensing and measuring preselected blood related parameters. The blood sample being analyzed is directly placed in contact with sensing means in the cartridge without intervening buffer solutions, exposure to air, etc. The unadulterated sample is analyzed within the cartridge and the measurement output therefrom is communicated to means outside the cartridge where it can be displayed, be analyzed further, be transmitted to a remote location, etc. The cartridge and its contents do not require on site calibration or a warm up period. This feature allows the system to be used by personnel not necessarily trained in calibrating sophisticated electronic equipment and facilitates rapid data output, particularly vital in critical care and emergency treatment situations.

20 Claims, 2 Drawing Sheets

METHODS AND APPARATUS FOR DIRECTLY SENSING AND MEASURING BLOOD RELATED PARAMETERS

This application is a continuation of application Ser. No. 547,381, filed July 3, 1990, pending, which is a continuation of Ser. No. 264,614, filed Oct. 31, 1988, abandoned.

FIELD OF THE INVENTION

The invention relates generally to methods and apparatus for sensing and measuring blood related parameters associated with a blood sample. More particularly, the invention relates to methods and apparatus for directly performing both of the aforementioned sensing and measurement functions on said sample utilizing disposable cartridge means.

DESCRIPTION OF THE RELATED ART

Conventionally, blood samples are gathered using techniques such as the well known VACUTAINER drawing system, hepronized syringe systems and finger/heel prick systems using capillary tubes.

For example, a blood sample could be obtained by making a small incision on the scalp and placing a capillary tube in the proximity of the incision whereby the blood is drawn up into the interior portions of the tube through capillary action.

Commonly used clinical devices for measuring blood related parameters, such as pH, include the blood gas analyzer manufactured by Corning Medical Corporation and the PHM71 Mk2 acid base analyzer from Radiometer Copenhagen. According to the prior art, the sensing surface of an electrode is placed in contact with the blood, which in turn is contacting a reference electrode via an electrolyte junction. The system is maintained at a preselected temperature by way of a relatively complex circulating heated water bath. Older analyzers required two point calibration necessitating relatively sophisticated electronics normally used by trained personnel.

Such analyzers generally require the transfer of the blood sample from a capillary tube to a receptacle in the instrument. As is known in the art, if any ambient air mixes with the blood sample, there is a possibility of contaminating the sample during the transfer from the original collecting device to the instrument.

Since such analyzers are complex and costly devices, they are typically located only in the hospital laboratory where they are operated by skilled technicians. As a result, there is often considerable delay between the time of taking the blood sample until the results from the lab are received. Of course, such delays are undesirable in emergency situations.

Many of these problems, however, are solved by the method and apparatus disclosed in U.S. Pat. No. 4,272,245, to Diamond et al, which discloses the broad concept of utilizing a disposable cartridge containing indicating and reference electrodes. A common electrolytic solution is used to establish a one point calibration factor and also serves as an electrolytic bridge during measurement of the sample. The sample is collected in a capillary tube and the cartridge is adapted to receive the blood sample directly from the tube. The capillary tube is slipped over the indicating electrode so that the blood displaces the solution and covers the indicating electrode. The electrical properties between the two electrodes are again measured and used to calculate the electrochemical activity (e.g., pH) of the sample in conjunction with the previously measured calibration factor.

A further improvement on the Diamond patent is disclosed by Enzer et al in U.S. Pat. No. 4,336,121 issued June 22, 1982. Enzer et al builds on the disposable cartridge concept and addresses the problem of quickly bringing and accurately maintaining the liquid sample at a predetermined temperature during the measurement process.

According to Enzer et al, thermally conductive means on the cartridge housing is adapted for receipt of a sensor for sensing the temperature of the liquid. The cartridge is designed to be slidably mounted in a socket attached to a pivoting door of an electronic measurement machine. The socket includes two opposing plates which come into contact with the cartridge. The temperature sensor is adapted to engage the thermally conductive means on the housing and provides an output signal to control the heating of the cartridge to quickly bring the components in the cartridge to a desired temperature.

Enzer et al employs an ampule containing an electrolyte solution which rests in a trough in the cartridge. Means are provided for breaking the capsule when the door is pivoted to the closed position. A sensing arrangement is provided for detecting the condition of the ampule and serves to trigger a calibration measurement when the capsule is broken to cover the electrodes with the solution. A forced air heater system is recommended by Enzer et al to keep the cartridge at a preselected temperature level to permit accurate measurement of the parameters being measured.

The Enzer et al system, like Diamond, requires calibration measurements and a warm up period because their cartridges use buffer solutions that need to be maintained at a specific temperature level. The aforementioned prior art systems are also problematic in that the blood sample must be mixed with the buffer solution and as a result parameter measurement is, at best, indirect and based on a sample adulterated by support media.

The prior art is devoid of a blood parameter measurement system that is capable of either directly or indirectly collecting a blood sample and directing it to a predetermined portion of the sensing and measuring device (in unadulterated form) where the unadulterated sample is directly analyzed.

Accordingly, it would be desirable to be able to analyze blood samples taken directly from the patient (or provided indirectly), via a sensing and measuring device that works on the unadulterated sample directly and does not requiring calibration or a warm up period. Such a device would facilitate use by personnel not trained to calibrate the equipment and allow rapid feedback regarding the parameter being measured.

Additionally, it would be desirable to be able to measure parameters associated with blood using disposable means that prevent adulteration of the sample from contact with the air or contact with a buffering solution.

Further yet, it would be desirable to be able to perform both the sensing and measurement of blood related parameters inside the disposable means to thereby eliminate the need for sophisticated, expensive support equipment traditionally utilized to perform the measuring function.

Realization of these desirable features would facilitate quick and accurate measurement, either in the laboratory or directly at a patient's bedside, of desired parameters and allow the speedy processing and output of accurate data, particularly vital to the treatment of critical care and Emergency Room patients.

SUMMARY OF THE INVENTION

It is therefore an object of the invention to both sense and measure blood related parameters within a disposable cartridge not requiring sophisticated support equipment to perform the measuring function.

It is a further object of the invention to sense and measure blood related parameters directly from blood samples unadulterated by any type of buffering solution or airborne contaminants.

It is still a further object of the invention to be able to perform the aforesaid sensing and measuring utilizing disposable means that does not require calibration or a warm up period to thereby provide the potential for more rapid feedback without the need for skilled operators.

According to the invention, the aforesaid objectives are achieved by locating means for performing both of the aforesaid sensing and measuring functions within a disposable cartridge within which an unadulterated blood sample is directly placed in proximity to the sensing means. The cartridge itself contains a vacuum chamber that helps with sample introduction while negating the prospect of contamination of the sample by exposure to air. Since no buffer solution is utilized, no warm up period is required. Precalibration of the disposable sensing and measuring devices themselves allows for use of the sensing and measuring system by personnel not necessarily trained in calibrating sophisticated electrical equipment.

Furthermore, according to the preferred embodiment of the invention, the disposable cartridges (containing the blood sample from which a preselected parameter is being sensed and measured) may be inserted into or otherwise coupled to relatively unsophisticated support equipment, such as an output device for conveniently reading measured parameters in a convenient format. As an example, the support equipment might contain LEDs for producing a digital display.

The invention features the precalibrated sensor and measurement means contained in a disposable cartridge; accurate means for sensing and measuring blood related parameters without performing on site calibration; parameter measurements that are based on the use of unadulterated blood samples; and a total system concept that includes relatively unsophisticated support equipment to conveniently output data.

These and other objects and features of the invention will be recognized by those skilled in the art upon reviewing the detailed description set forth hereinafter in conjunction with the Drawing.

DETAILED DESCRIPTION

Figure 1:
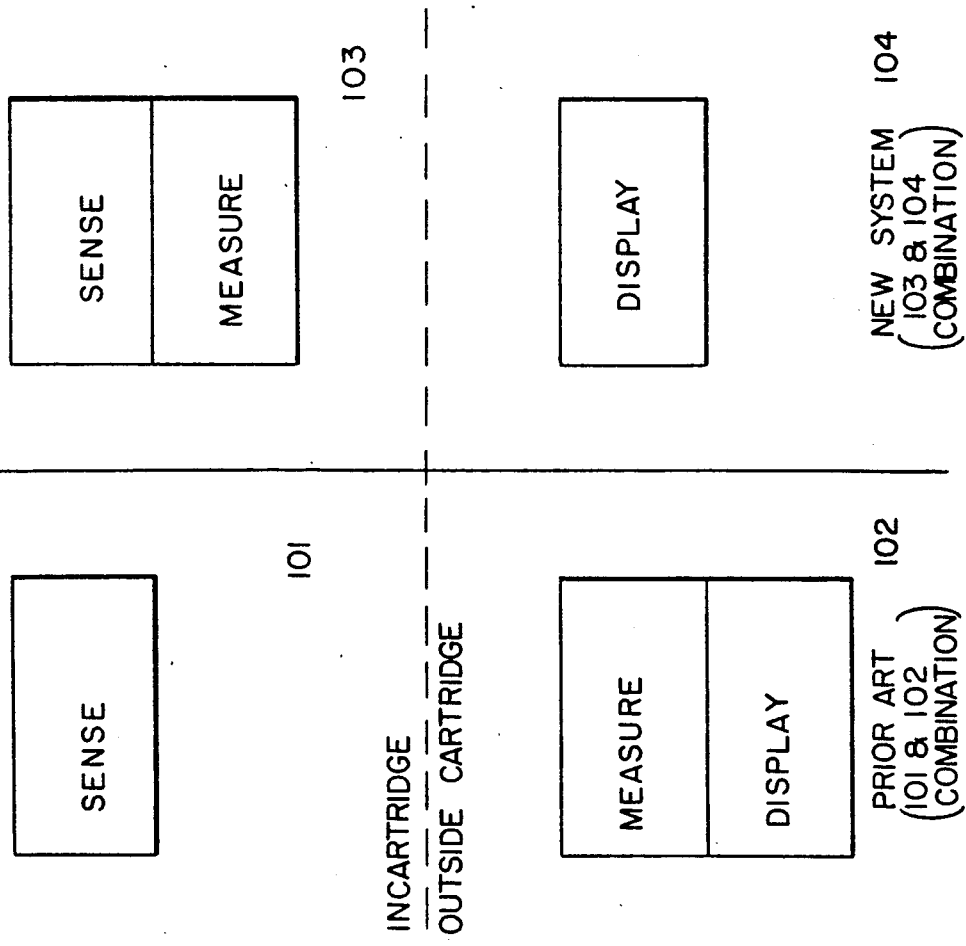
FIG. 1 depicts a comparison of the functions performed with the cartridge of known cartridge parameter sensing systems versus the functions performed within the cartridge that achieves the objects of the invention.

FIG. 1 shows in block diagram form a characterization of one of the key conceptual differences between known systems for sensing and measuring blood related parameters and the system disclosed herein.

The prior art systems, as typified by the teachings of the aforementioned Diamond and Ezer et al patents, sense predetermined parameters associated with blood (like pH) using a disposable cartridge that contains a pair of electrodes acting as the sensing means.

Section 101 of FIG. 1 shows the sensing taking place within the cartridge itself. The measurement and display functions are shown, in section 102 of FIG. 1, as taking place outside the cartridge in an external measurement and display device.

FIG. 1 goes on to show that, in accordance with the teachings of the invention, both the parameter sensing and measurement functions are to be performed within the disposable cartridge (section 103 of FIG. 1) and that the display function is handled outside the cartridge (as shown by section 104 of FIG. 1) or even in some cases (not depicted) within the cartridge as well.

The development of new and improved sensing and measuring devices, along with their miniaturization, makes the new measurement system concept feasible and economical.

In addition, the ability to calibrate the sensing and measuring device (or devices) at the factory for one time use, eliminates the need for complex multiple usage calibration required by the prior art.

According to the invention, a blood sample is directed, in unadulterated form, to the sensing and measuring means located with the disposable cartridge.

Figure 2:
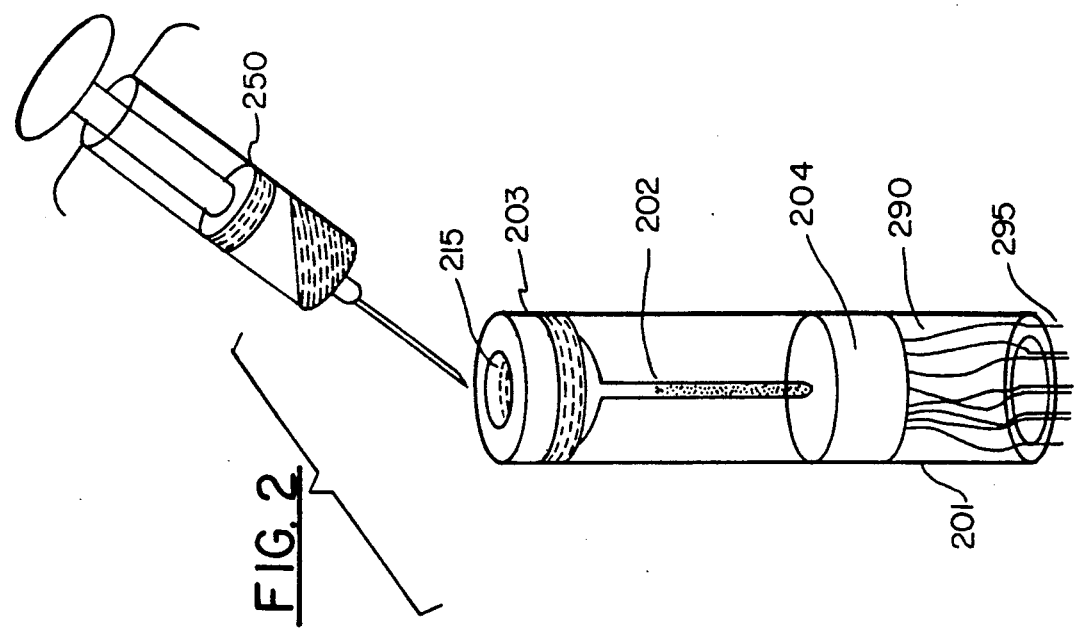
FIG. 2 depicts an embodiment of a disposable cartridge that achieves the objects of the invention.

FIG. 2 depicts an example of a cartridge fashioned in accordance with the teachings of the invention. The illustration in FIG. 2 is not to scale, but exaggerated to illustrate the various components of the invention more clearly.

The cartridge houses a complete sensing and measuring system and also serves as the blood introduction port and sampling chamber. As indicated hereinbefore, use of the evacuated chamber helps in sample introduction and negates possible contamination by air.

Cartridge 201 of FIG. 2 is similar in shape and operation to well known VACUTAINER blood sample tubes. These tubes are typically evacuated (partial vacuum) and the sample is collected by piercing the top seal with a syringe. In disposable cartridge 201, blood is directed to the sensor housing via a capillary tube 202. The capillary tube could be omitted if seal 203 were fabricated as a part of sensor and measurement device housing 204. According to the preferred embodiment of the invention, sensor and measurement device housing 204 is sized to hold a 50 microliter blood sample, and utilizes well known pressure relief means, such as a pressure relief valve, to prevent damage to the seal and sensor/measurement components if over-filling is attempted. All surfaces of the cartridge and housing 204 which come in contact with blood should be heparinized to prevent clotting.

FIG. 2 depicts hypodermic needle 250 being used to introduce blood through a relatively thin portion of seal 203, shown as portion 215 in FIG. 2. According to one embodiment of the invention, seal 203 is simply a rubber stopper.

Capillary tube 202 is shown in FIG. 2 to direct the injected blood sample to sensor and measurement housing 204. No buffer solution or air contact is made with the blood sample to be analyzed.

Output lead wires from housing 204, shown as lead wires 290 in FIG. 2, are shown as means for outputting measurements calculated within cartridge 201. The lead wires are shown coupled to electrical connector means such as contact pins 295. According to this illustrative embodiment the cartridge is designed to be coupled to a display device. A means of accomplishing this will be set forth hereinafter.

According to one embodiment of the invention the cartridge is plastic. Glass would also be a suitable material and the invention is specifically not meant to be limited by the composition of the housing.

The lead wires shown in FIG. 2 could be bundled or unbundled wires per se, fiber optic paths, or in fact, any means for coupling the measurements output by the device or devices in housing 204, to a means for displaying or otherwise using the output from the tube. Thus connector means, such as contact pins 295, may be appropriate; a single pin for bundled leads may be appropriate; or in fact any other means of communications between the inside of the cartridge and devices located outside the cartridge may be contemplated by those skilled in the art.

The types of sensing and measuring devices that may be housed within housing 204 are varied. For example, temperature sensing and measuring devices, in the form of off the shelf thermometers, are known that when bathed with a liquid sample (e.g. blood) will both sense and measure the temperature of the sample. The measured temperature output could easily be directed, via lead wires 290 and contact pins 295, to a display device where the temperature could be read out on a digital display. In fact, if the sensor housing were transparent and the thermometer means had degree marks thereon, it would be possible to sense, measure and display the output, all within the cartridge.

Other devices for sensing a variety of blood related parameters of interest to the medical profession, could be installed in housing 204. In particular, for analyzing blood gases rapidly, one skilled in the art would contemplate housing pH, Pco2 and Po2 sensing and measuring devices in the cartridge sensor and measurement housing. The actual device or devices contained in the housing per se is not meant to be a limiting factor regarding the scope of the invention. The ability to house devices that perform both the sensing and measurement function on an unadulterated blood sample, within a disposable cartridge, is a principal object of the invention per se.

Figure 3:
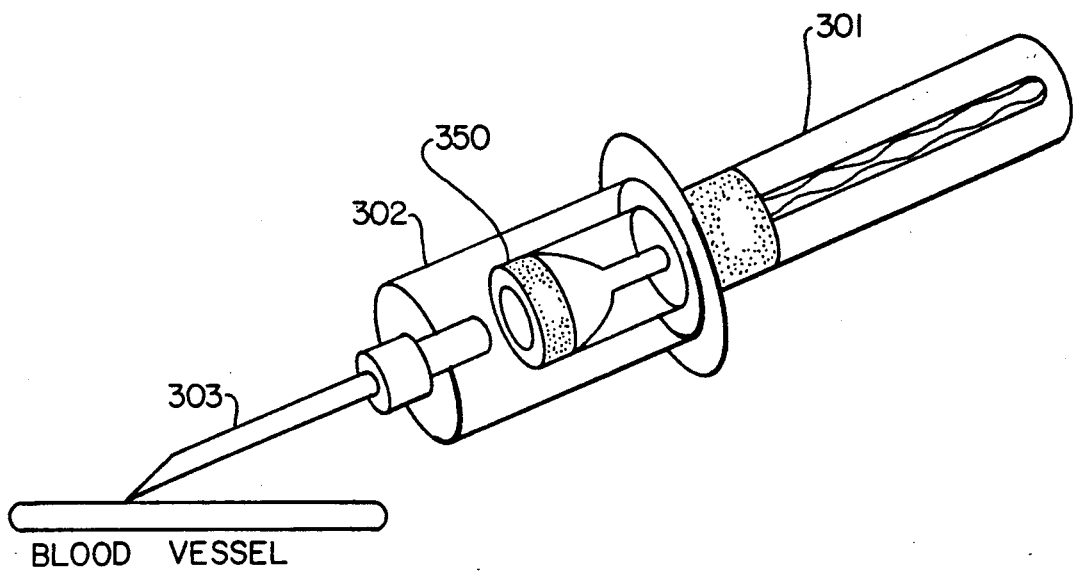
FIG. 3 depicts the cartridge of FIG. 2 being utilized in conjunction with a VACUTAINER drawing system.

FIG. 3 goes on to depict how the cartridge of FIG. 2 could be used in conjunction with a VACUTAINER drawing system. FIG. 3 shows the cartridge, 301, being inserted into VACUTAINER device 302 and that a needle, 303, can be used to directly convey blood from a patient's blood vessel to (and through) the stopper atop cartridge 301 (the stopper is shown in FIG. 3 as component 350).

The apparatus depicted in FIG. 3 illustrates how blood can be conveyed directly from the patient to the measuring and sensing cartridge in a manner that assures that unadulterated blood is supplied to the cartridge and device(s) located therein. One skilled in the art will readily appreciate that the disposable cartridge can be used with or without the VACUTAINER drawing system, as seen in a comparison of FIGS. 2 and 3.

Figure 4:
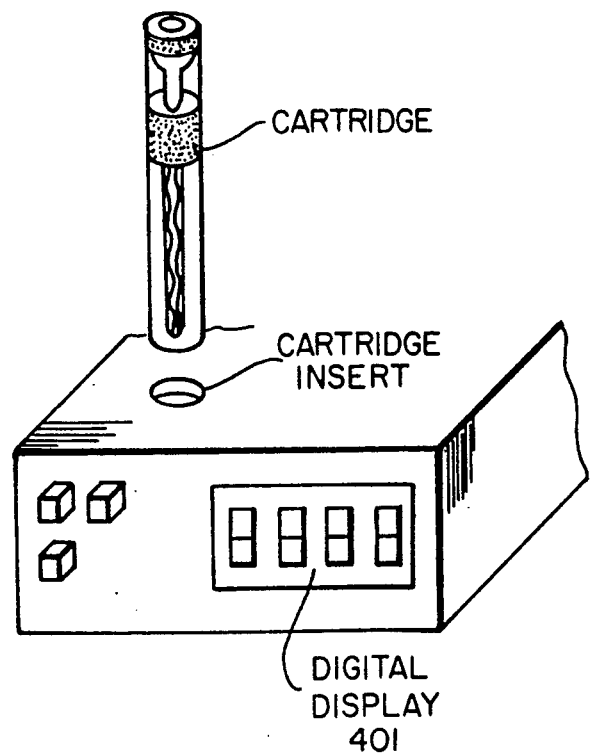
FIG. 4 depicts the cartridge of FIG. 2 being utilized in conjunction with a digital read out device.

FIG. 4 depicts an example of how the cartridge of FIG. 2 may be used in conjunction with a display device to provide a readout of the sample analyzed. Devices are known which accommodate an inserted cartridge (such as the prior art cited specifically herein). The device depicted in FIG. 4 simply takes the electrical output on lead wires 290 and contact pins 295, and couples same to an LED digital display. Device 401 of FIG. 4 could conceivably contain more sophisticated electronics, processing equipment, transmission equipment, etc., to handle the output of the cartridge in many ways. The type of output device per se is not important; that the cartridge has a measurement output that can be coupled to external devices and be used in a variety of ways, is important to an understanding the invention.

What has been described is a disposable cartridge device that can be used to both sense and measure blood related parameters, where the sample being analyzed is directly placed in contact with the sensor without intervening buffer solutions, exposure to air, etc. The unadulterated sample is analyzed within the cartridge and the measurement output therefrom is communicated to means outside the tube for the purposes of display, further analysis, transmission to a remote location, etc.

The cartridge does not require calibration or a warm up period. Multiple uses are not intended, and therefore a new cartridge may be used for analyzing subsequent samples and these too do not require cleaning, warm up or calibration.

Having described in detail methods and apparatus for directly sensing and measuring blood related parameters within a disposable cartridge, methods for obtaining an unadulterated blood sample for analysis, etc., one of ordinary skill in the art will readily appreciate that the objectives of the invention, set forth hereinbefore, have been met.

The foregoing description of a preferred embodiment and illustrative examples of the novel methods and apparatus has been presented for the purposes of illustration and description only. It is not intended to be exhaustive or to limit the invention to the precise form disclosed, and obviously many modifications and variations are possible in light of the above teaching.

The embodiment and examples set forth herein were presented in order to best explain the principles of the instant invention and its practical application to thereby enable others skilled in the art to best utilize the instant invention in various embodiments and with various modifications as are suited to the particular use contemplated.

It is intended that the scope of the instant invention be defined by the claims appended hereto.

What is claimed is:

1. A method for directly sensing and measuring blood related parameters in a non-reuseable disposable container, the method comprising the steps of:
    (a) introducing an unadulterated blood sample into non-reuseable disposable encapsulating means for performing both the sensing and measuring of a preselected blood related parameter;
    (b) directing said blood sample to means within said encapsulating means for performing both the sensing and measuring of said preselected blood related parameter;

(c) sensing and measuring said preselected parameter entirely within said encapsulating means directly from said unadulterated blood sample; and (d) outputting, from said encapsulating means, the measured value of said parameter.

2. A method as set forth in claim 1 further comprising the step of heparinizing the interior surfaces of said encapsulating means to thereby prevent the clotting of blood introduced therein.

3. A method as set forth in claim 1 wherein said encapsulating means is a disposable cartridge.

4. A method as set forth in claim 3 further comprising the step of locating said sensing and measuring means within a housing located within said disposable cartridge.

5. A method as set forth in claim 4 further comprising the step of heparinizing the interior surfaces of said cartridge and the housing located therein to prevent the clotting of blood introduced therein.

6. A method as set forth in claim 5 further comprising the step of releasing pressure from said cartridge and housing via pressure relief valve means whenever overfilling of the volume within said cartridge and housing is attempted.

7. A method as set forth in claim 1 wherein said step of outputting is performed utilizing at least one lead wire coupled between the sensing and measuring device located within said housing and means for communicating said measured value to the outside of said encapsulating means.

8. A method as set forth in claim 7 wherein said means for communicating is at least one contact pin.

9. A method as set forth in claim 1 further comprising the step of displaying said measured value.

10. Apparatus for directly sensing and measuring blood related parameters, comprising non-reuseable disposable encapsulating means including means for performing both the sensing and measuring of a preselected blood related parameter entirely within said encapsulating means directly from an unadulterated blood sample.

11. Apparatus as set forth in claim 10 wherein said encapsulating means is a portable cartridge.

12. Apparatus as set forth in claim 10 wherein said encapsulating means further comprises pressure relief means.

13. A system for obtaining an unadulterated blood sample, analyzing said sample to sense and measure a preselected parameter associated therewith, and output a signal indicative of the measured value of said parameter, said system comprising:

(a) non-reuseable disposable encapsulating means including means for performing both the sensing and measuring of said parameter entirely within said encapsulating means;

(b) means for introducing an unadulterated blood sample into said encapsulating means;

(c) means for assuring the blood sample introduced into said encapsulating means is conveyed, in unadulterated form, to said means for sensing and measuring so that said sensing and measuring may be performed directly from an unadulterated blood sample;

(d) output means, coupled to said means for sensing and measuring, for outputting a signal indicative of the measure of said parameter;

(e) means, coupled between said output means and the outside of said encapsulating means, for communicating said output signal to display means; and (f) display means for displaying the value of said measured parameter as a function of the value of said signal.

14. A system as set forth in claim 13 wherein said disposable encapsulating means is a portable cartridge.

15. A system as set forth in claim 13 wherein said means for introducing is a syringe.

16. A system as set forth in claim 13 wherein said means for introducing is a drawing system to which said encapsulating means may be coupled so that drawn blood is directly communicated from the patient to said encapsulating means.

17. A system as set forth in claim 13 further comprising means for sealing said encapsulating means, which permits the introduction of an unadulterated blood sample into said encapsulating means through a puncturable portion of said means for sealing.

18. A system as set forth in claim 13 wherein said output means comprises at least one lead wire coupled between said means for sensing and measuring and said means for communicating.

19. A system as set forth in claim 18 wherein said means for communicating comprises at least one contact pin.

20. A system as set forth in claim 13 wherein said encapsulating means further comprises pressure relief means.

* * * * *